(12) United States Patent
Schmittmann et al.

(10) Patent No.: US 10,900,937 B2
(45) Date of Patent: Jan. 26, 2021

(54) CONTINUOUS AND SEPARATING GAS ANALYSIS

(71) Applicant: bentekk GmbH, Hamburg (DE)

(72) Inventors: Matthias Schmittmann, Hamburg (DE); Johannes Weber, Hamburg (DE); Arne Jünemann, Hamburg (DE); Paul Weber, Berlin (DE)

(73) Assignee: bentekk GmbH, Hamburg (DE)

( * ) Notice: Subject to any disclaimer, the term of this patent is extended or adjusted under 35 U.S.C. 154(b) by 281 days.

(21) Appl. No.: 15/768,085

(22) PCT Filed: Oct. 11, 2016

(86) PCT No.: PCT/EP2016/074315
§ 371 (c)(1),
(2) Date: Apr. 13, 2018

(87) PCT Pub. No.: WO2017/064047
PCT Pub. Date: Apr. 20, 2017

(65) Prior Publication Data
US 2018/0335407 A1 Nov. 22, 2018

(30) Foreign Application Priority Data
Oct. 13, 2015 (DE) .................... 10 2015 219 838

(51) Int. Cl.
*G01N 30/32* (2006.01)
*G01N 30/16* (2006.01)
*G01N 30/38* (2006.01)
*G01N 33/00* (2006.01)
*G01N 30/88* (2006.01)
(Continued)

(52) U.S. Cl.
CPC ............. *G01N 30/32* (2013.01); *G01N 30/16* (2013.01); *G01N 30/38* (2013.01); *G01N 30/88* (2013.01);
(Continued)

(58) Field of Classification Search
CPC .... G01N 30/32; G01N 30/88; G01N 33/0031; G01N 33/0047; G01N 30/16;
(Continued)

(56) References Cited

U.S. PATENT DOCUMENTS 6,165,251 A  12/2000 Lemieux et al.
7,273,517 B1 * 9/2007 Lewis ................ G01N 30/6095
                                                       73/23.39
(Continued)

OTHER PUBLICATIONS

International Search Report and Written Opinion dated Dec. 22, 2016, directed to International Application No. PCT/EP2016/074315; 20 pages.
(Continued)

*Primary Examiner* — Randy W Gibson
*Assistant Examiner* — John M Royston
(74) *Attorney, Agent, or Firm* — Morrison & Foerster, LLP

(57) ABSTRACT

A portable gas analysis apparatus for conducting a gas flow, in particular for highly volatile compounds, includes a seeker measurement path and a separation measurement path. The seeker measurement path extends from a sample gas inlet opening to a first air exit opening, wherein a connecting path branches off from the seeker measurement path to a separation measurement path, and said separation measurement path extends from the connecting path to a second air exit opening and is connected to a carrier gas inlet opening, wherein the gas analysis apparatus has a control element which is designed for reversing the gas flow in the connecting path.

17 Claims, 10 Drawing Sheets

(51) Int. Cl.
  *G01N 30/00* (2006.01)
  *G01N 30/02* (2006.01)
(52) U.S. Cl.
  CPC ..... *G01N 33/0031* (2013.01); *G01N 33/0047* (2013.01); *G01N 2030/0095* (2013.01); *G01N 2030/025* (2013.01); *G01N 2030/328* (2013.01); *G01N 2030/884* (2013.01)
(58) Field of Classification Search
  CPC ............. G01N 30/38; G01N 2030/328; G01N 2030/0095; G01N 2030/025; G01N 2030/884
  See application file for complete search history.

(56) References Cited

U.S. PATENT DOCUMENTS

| | | |
|---|---|---|
| 2005/0284209 A1 | 12/2005 | Tipler et al. |
| 2009/0101017 A1 | 4/2009 | Furukawa |
| 2011/0005300 A1 | 1/2011 | Wang et al. |
| 2011/0259081 A1 | 10/2011 | Chou et al. |
| 2012/0143515 A1* | 6/2012 | Norman ............. G01N 33/0073 702/24 |

OTHER PUBLICATIONS

Sielemann. (Nov. 1999). "Detektion flüchtiger organischer Verbindungen mittels Ionenmobilitätsspektrometrie und deren Kopplung mit Multi-Kapillar-Gas-Chromatographie," Vorn Fachbereich Chemie der Universitat Dortmund zur Erlangung des akademischen Grades eines Doktors der Naturwissenschaften genehmigte Dissertation; 140 pages.

Office Action dated Oct. 2, 2020, directed EP Application No. 16781742.8; 7 pages.

\* cited by examiner

CONTINUOUS AND SEPARATING GAS ANALYSIS

REFERENCE TO RELATED APPLICATIONS

This application is a national stage application under 35 USC 371 of International Application No. PCT/EP2016/074315, filed Oct. 11, 2016, which claims the priority of German Application No. 10 2015 219 838.3, filed Oct. 13, 2015, the entire contents of each of which are incorporated herein by reference.

FIELD OF THE INVENTION

The invention relates to a portable gas analysis apparatus for conducting a gas flow, in particular for highly volatile compounds.

BACKGROUND OF THE INVENTION

Highly volatile organic substances are often hazardous to health. For this reason, it is necessary for legally stipulated maximum values for the concentration thereof to be adhered to in the environment and around plant facilities. The measurement of the concentration of the highly volatile compounds may be performed using mobile measurement appliances.

The measurement for the detection of the individual concentrations of the highly volatile compounds in a sample gas mixture requires a relatively long period of time of at least several minutes. A very long time is therefore required for spatially resolved measurement of the individual concentrations in large areas or large buildings. For this reason, a fast integration measurement (approximately 2 seconds) is firstly performed in order to detect the locations at which highly volatile compounds are present in a relatively high concentration. It is known internally that, in the case of mobile measurement appliances, a gas flow of the sample gas mixture is conducted to a detector which detects the total concentration of the highly volatile compounds in the sample gas. If highly volatile compounds are found, the gas flow of the sample gas mixture is conducted by way of valves to another detector which measures the individual concentrations of the highly volatile compounds in the sample gas.

Said known measurement appliances have the disadvantage that, for the duration of the measurement of the individual concentrations, the seeking of further locations at which relatively high concentrations of the highly volatile compounds could be present must be interrupted.

Conventional measurement appliances which permit a simultaneous measurement have, for each measurement mode, a separate measurement path with separate openings, blowers, valves and lines for the sample gas. Owing to this multiple structure, said measurement appliances are heavy and require intensive maintenance.

SUMMARY OF THE INVENTION

The invention is based on the object of realizing a gas analysis apparatus which is improved with regard to compactness and fast-acting capability, and which is expedient in terms of consumption and wear.

According to the invention, in the case of a portable gas analysis apparatus for conducting a gas flow, in particular for highly volatile compounds, which portable gas analysis apparatus comprises a seeker measurement path and a separation measurement path, it is provided that the seeker measurement path extends from a sample gas inlet opening to a first air exit opening, wherein a connecting path branches off from the seeker measurement path, and said separation measurement path extends from the connecting path to a second air exit opening and is connected to a carrier gas inlet opening, wherein a separation detector is arranged at the separation measurement path, wherein the gas analysis apparatus has a control element which is designed for reversing the gas flow in the connecting path.

Firstly, some expressions will be discussed in more detail:

A seeker measurement path is to be understood to mean the path of the sample gas mixture in the gas analysis apparatus over which the presence of highly volatile compounds is detected. The seeker measurement path serves for the seeking of the highly volatile compounds.

A separation measurement path is to be understood to mean the path of the sample gas mixture in the gas analysis apparatus over which the components of the mixture are separated in order to detect the individual concentrations. The separation measurement path thus serves for separating a gas mixture into its constituent parts in order to detect the concentrations of the individual compounds.

The invention is based on the concept of controlling the measurement of the individual concentrations of the highly volatile compounds by way of the direction of the gas flow in the connecting path. For as long as no measurement is being performed, carrier gas flows from the connecting path into the seeker measurement path. By virtue of the direction of the gas flow in the connecting path being reversed by way of the control element, a part of the sample gas mixture flows from the seeker measurement path via the branching connecting path into the separation measurement path, such that the individual concentrations can be measured. Here, the other part of the sample gas remains in the seeker measurement path, such that the search for the presence of highly volatile compounds can be continued. The gas flow may be generated by way of flow generator elements such as, for example, blower units and/or other suitable apparatuses such as flow directors and valves.

Here, no valve is required between the connecting measurement path and the seeker measurement path. The reversal of the gas flow is rather effected by way of a control element which controls the pressure ratios between the separation measurement path and the seeker measurement path. The control of the direction of the gas flow may be realized by way of a change in the pressure difference between the seeker measurement path and the separation measurement path.

During the search as regards whether highly volatile compounds are actually present at the measurement locations, the control element has the effect that the pressure in the separation measurement path is higher than that in the seeker measurement path. In this way, carrier gas flows from the carrier gas inlet opening through the connecting path into the seeker measurement path. The sample gas that flows through the sample gas inlet opening is thereby prevented from flowing into the separation measurement path. In the seeker measurement path, the sample gas can be analyzed for highly volatile compounds. In this case, the sample gas and the carrier gas escape through the first air exit opening.

If highly volatile compounds have been detected in the seeker measurement path, the control element can, preferably automatically, set the pressure ratios in the gas analysis apparatus such that a lower pressure prevails in the separation measurement path than in the seeker measurement path. In this way, a part of the sample gas is conducted from the seeker measurement path through the branching connecting path into the separation measurement path. In the separation measurement path, the concentrations of the individual compounds in the sample gas can be detected. In this case, the sample gas escapes through the second air exit opening.

Since only a part of the sample gas that flows through the seeker measurement path flows through the connecting path, the search for highly volatile compounds can be continued while the individual concentrations of the highly volatile compounds are detected. This accelerates the surveying of large areas or large buildings. The invention furthermore utilizes the measurement paths in an efficient manner, and thereby avoids the use of a multiple structure. This reduces the weight and the wear of the components of the gas analysis apparatus. Furthermore, owing to the omission of a valve between the connecting path and the seeker measurement path, the maintenance of the portable gas analysis apparatus is simplified, and the service life of the apparatus is lengthened, as the number of mechanical components is kept low.

It is advantageously provided that, in the seeker measurement path, there is arranged a seeker detector which is designed for the continuous detection of the presence of a group of highly volatile compounds, and which is preferably a photoionisation detector, a semiconductor gas detector or a heat conductivity detector.

The control element may advantageously be designed for automatically reversing the gas flow in the connecting path if the presence of highly volatile compounds is detected.

Furthermore, the separation detector is advantageously designed for determining the amount of highly volatile compounds and is preferably a gas chromatograph in combination with a photoionisation detector, a heat conductivity detector, a semiconductor gas detector or a mass spectrometer. For this purpose, it is expedient for the separation detector to comprise a separation column which is in the form of a multi-capillary column. Here, the separation column functions as a retention element through which the individual highly volatile compounds flow at different speeds. The multi-capillary leads to a greater gas volume flow (stronger signals) and consequently to lower detection limits. In conjunction with the shortness of the column (and its material condition), this leads to fast analysis. Thus, the determination of the concentration of a highly volatile compound takes place very quickly, and can be performed in less than 30 seconds. This is of great advantage in particular for portable gas analysis apparatuses in order to be able to quickly obtain measurement results directly on site.

The first air exit opening and the second air exit opening are preferably combined within one housing to form a common air exit opening. Thus, the separation measurement path and the seeker path utilize a common air exit opening. The gas analysis apparatus can thus be made even more compact, which can yield a considerable usage advantage in particular in the case of portable use.

It is expediently the case that an entire analytical path—formed by the seeker measurement path, the separation measurement path as far as the separation detector and the connecting path—is formed so as to be free from valves, that is to say without valves. With the omission of valves in said region, the risk of analysis-falsifying enrichment in the valve region is counteracted in an effective manner. Furthermore, it is thus possible for the measurement speed to be increased, and for wear to be reduced.

It is advantageously the case that a filter path branches off from the connecting measurement path, which filter path is connected to the carrier gas inlet opening, wherein a filter element is arranged in the filter path. The filter element is utilized for filtering highly volatile compounds out of the carrier gas flowing through the carrier gas inlet opening. The filtered carrier gas can thereafter be used as purging gas in the separation measurement path in order, between two measurements of the individual concentrations, to purge residues of the sample gas from the most recent measurement. If a higher pressure prevails in the separation measurement path than in the seeker path, the carrier gas from the carrier gas inlet opening can flow firstly through the filter element. The carrier gas flows subsequently through the separation measurement path. At the same time, the carrier gas can flow through the connecting path into the seeker measurement path. The filter path may be formed as a bypass with respect to the separation detector. If the pressure in the separation measurement path is lower than that in the seeker measurement path, no carrier gas passes from the filter path into the connecting path.

For this purpose, it is expediently provided that, in a first advantageous embodiment, the control element is in the form of a valve which is designed for opening and shutting off the filter path. In this case, after the shutting-off of the filter path, the carrier gas is conducted directly from the carrier gas inlet opening through the second air exit opening. In another embodiment, the carrier gas flow may be blocked at the carrier gas inlet opening, such that the carrier gas does not flow into the gas analysis apparatus or into the filter path in the first place.

In a second advantageous embodiment, the control element is in the form of a regulable blower unit at the carrier gas inlet opening, at the first air exit opening and/or at the separation detector. By means of the regulated increase or decrease in blower power, the pressure in the seeker measurement path and/or in the separation measurement path is influenced. With the regulable blower unit, it is thus possible to adjust the pressure in the separation measurement path in relation to the seeker measurement path. Here, it is possible for either the pressure in the seeker measurement path or the pressure in the separation measurement path to be changed. If regulable blower units are arranged both in the seeker measurement path and in the separation measurement path, it is possible for the pressures in the seeker measurement path and in the separation measurement path to be varied oppositely, in such a way that the gas flow direction in the connecting path is reversed. It may however also be provided that pressure differences along the gas paths of blower units are determined, and a control element is formed as a valve, the position of which determines the direction of the gas flow in the connecting path. For this purpose, it is furthermore expedient if, at the carrier gas inlet opening, there is arranged a throughflow or pressure difference sensor, wherein the power of the blower unit at the separation detector is regulated in a manner dependent on the measurement of the throughflow or pressure difference sensor. It is thus possible for the regulation of the blower units to be regulated on the basis of the carrier gas throughflow. In both embodiments, the control of the gas flows in the gas analysis apparatus is simplified, as it is possible for complex valve and blower controllers to be omitted.

In further embodiments, the seeker may be implemented without a seeker detector, in particular if a continuous measurement is superfluous, for example because the local measurement points are already preselected or prescribed, in the case of regular measurements and/or in the case of measurements of samples from closed-off volumes. In such situations, the seeker permits a delay-free triggering of the separation measurement as soon as the appliance has been switched on and has warmed up. Sample gas is drawn into the seeker continuously, which sample gas is, upon triggering of the measurement, injected from the gas flow in the seeker by the connecting path into the separation detector. Before and after the injection, filtered carrier gas flows through the connecting path into the seeker, whereby the connecting path is purged. By means of this counter-purging, on the one hand, and the continuous gas flow into the sample gas inlet opening, on the other hand, an enrichment of volatile compounds in the seeker and in the analytical path is prevented, and any deposits are blown out. Without the seeker, the counter-purging would blow carrier gas out of the sample gas inlet opening and would thus dilute a closed-off sample volume. By means of the seeker, the gas flow at the sample gas inlet opening is always directed into the appliance, such that the sample is not diluted and contaminated.

In a further usage example, in the case of which a seeker detector can be dispensed with, a person operates the appliance, which draws in the sample via a hose, which is moved by a second person, for example a diver in a tank, to the location of the measurement. In this usage situation, by means of a higher power of the blower at the seeker, the continuous gas flow is realized through a longer hose into the sample gas inlet opening, such that, in the seeker, the correct sample concentration takes effect with a short delay, and the sample can be injected from the seeker into the separation detector at any time. In this example, the combination of seeker and separation measurement path without seeker detector is procedurally advantageous. In other cases, dispensing with the seeker detector is advantageous, because the production costs and structural space requirement without this component are lower.

Further advantages of the seeker, both with and without a seeker detector, are faster reaction times and reduced wear resulting from contamination of the separation detector. The blowers at the appliance can, owing to the seeker, be operated continuously, whereby the settling of the power is limited to a short warm-up phase. In one advantageous embodiment, the power may thereafter be stabilized or modulated by means of a regulation loop with a throughflow sensor. By means of the seeker, the reversal of the gas flow and thus injection for the separation measurement can be triggered without a warm-up, prior purging or similar method steps. During operation before and after the injection, the appliance is self-cleaning in the seeker path, in the connecting path and, after the end of the separation measurement, also in the separation measurement path, which are all advantageously designed without valves, at which enrichment of substances occurs to an increased extent. Through the avoidance of fouling of the gas paths that is thus achieved, wear is reduced, and the service life of the components is lengthened. The continuous operation of the blowers also stabilizes the generation of heat in the appliance, whereby sudden warming in the region of the separation detector during the measurement, which for instance in the case of a gas chromatograph would heavily distort the results, does not occur.

Furthermore, the gas analysis apparatus advantageously has a location finding module which is designed for determining the geographical coordinates of the gas analysis apparatus and which is preferably connected to the control element by way of a signal connection. The location coordinates may in this case expediently be stored, together with the measurement data regarding the total and individual concentrations, in a memory unit.

The gas analysis apparatus advantageously comprises an internal evaluation unit which is designed for evaluating the measurement data.

The invention also relates to a system which has a portable gas analysis apparatus according to the above description, having an internal evaluation unit, and an external evaluation unit, wherein, according to the invention, it is provided that the internal evaluation unit and the external evaluation unit are designed for exchanging control commands and measurement data by way of a wireless signal connection. An external evaluation unit can be easily upgraded, and generally has higher processing power, and more advanced display possibilities, than evaluation components integrated into the appliance.

Furthermore, the invention relates to a gas analysis method using a portable gas analysis apparatus according to the above description, having the steps: setting a higher pressure in the separation measurement path than in the seeker measurement path, detecting the presence of one highly volatile compound from a group of highly volatile compounds, setting a lower pressure in the separation measurement path than in the seeker measurement path, separating the individual members of the group of highly volatile compounds, determining the amount of the separated highly volatile compounds, wherein the detection of the presence of the highly volatile compounds is preferably performed continuously during the separation and determination processes.

Here, an interrogation signal is advantageously automatically transmitted in response to the detection of the presence of highly volatile compounds. It is advantageously the case that a lower pressure is set in the separation measurement path than in the seeker measurement path after the transmission of an interrogation signal. It is expediently provided that the geographical coordinates of the location at which the separation and the determination of the amount are performed are determined and stored.

BRIEF DESCRIPTION OF THE DRAWINGS

The invention will be discussed in more detail below with reference to the appended drawing on the basis of advantageous exemplary embodiments. In the drawing.

DETAILED DESCRIPTION OF THE INVENTION

Figure 1A:
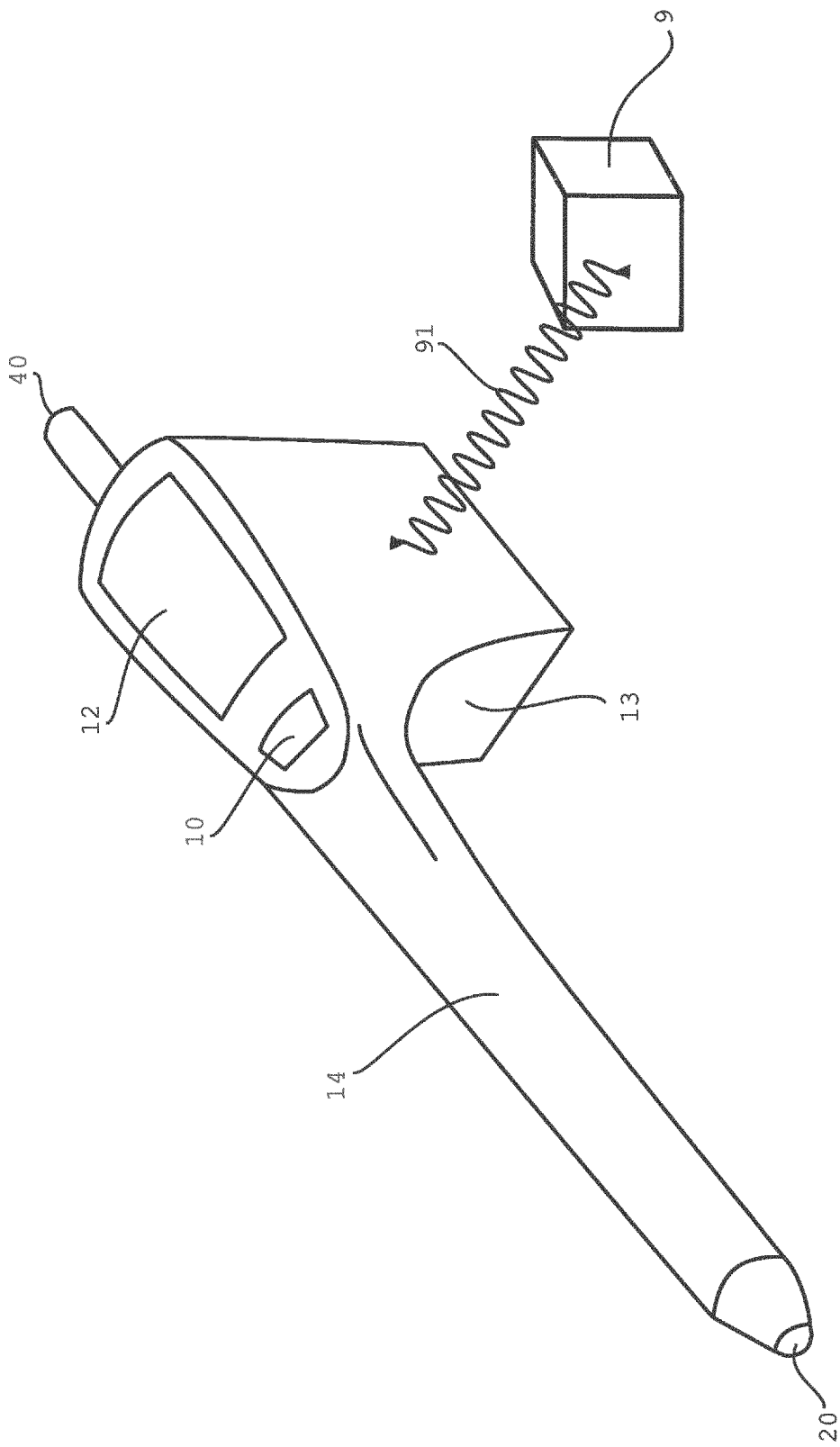
FIGS. 1a-c show perspective views of various exemplary embodiments of a portable gas analysis apparatus with external evaluation unit.

The portable gas analysis apparatus is designated as a whole by the reference sign 1. The gas analysis apparatus 1 has a housing 13 on which there are arranged a sample gas inlet opening 20 and a carrier gas inlet opening 40. In a first embodiment, as illustrated in FIG. 1a, the gas analysis apparatus has a compact housing 13. Furthermore, the compact housing 13 has an operating element 10 and a display screen element 12 and is connected to an external evaluation unit 9 via a wireless connection 91. The operating element 12 and display screen element 12 may preferably be of combined design, in the form of a touch-sensitive display ("touch screen"). It is optionally possible for the housing 13, as illustrated in FIG. 1a, to be of pistol-shaped form, with the projection 14 being in the form of a shaft. This is however not necessary; the housing may also be of cuboidal form for the benefit of even greater compactness.

Figure 2A:
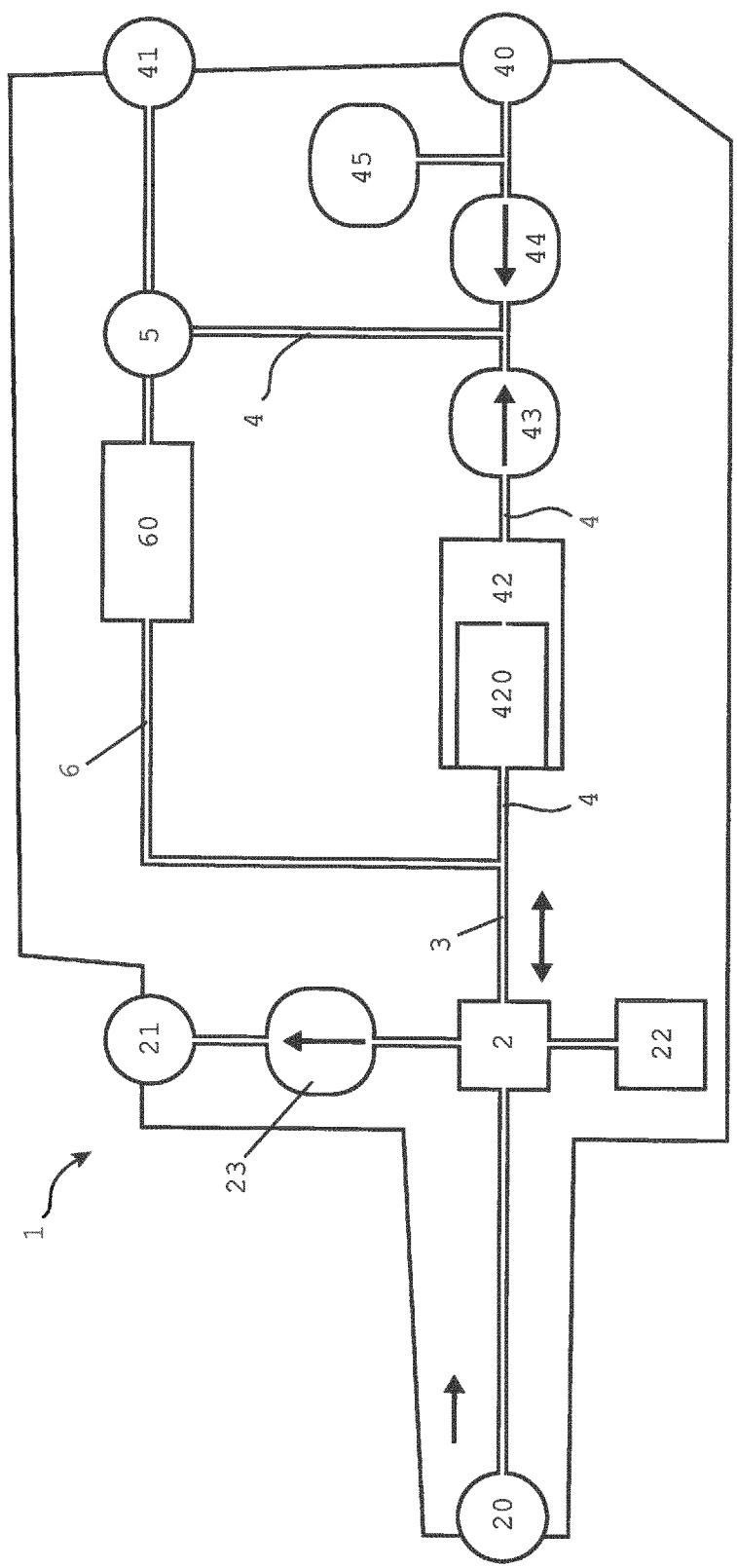
FIGS. 2a-c show schematic illustrations of the components of a portable gas analysis apparatus according to the invention, with different embodiments of the control element.

In a further embodiment, the operating element 10 and display screen element 12 are arranged externally, preferably together with the evaluation unit 9 in a second housing 92. In a first preferred embodiment as per FIG. 2a, a seeker measurement path 2 extends from the sample gas inlet opening 20 to a first air exit opening 21. At the first air exit opening 21 there is furthermore arranged a first regulable blower unit 23 as a flow generator element. The first regulable blower unit 23 generates a gas flow in the direction of the first air exit opening 21. Thus, by means of the first regulable blower unit 23, sample gas is drawn in from the sample gas inlet opening 20, which sample gas is conducted via the seeker measurement path 2 to the first air exit opening 21. The seeker measurement path 2 furthermore comprises a seeker detector 22. The seeker detector 22 is a photoionisation detector. A part of the sample gas flow is conducted to the seeker detector 22. Here, the seeker detector 22 continuously performs a measurement with which it can be detected whether highly volatile compounds are contained in the sample gas.

A connecting path 3 branches off from the seeker measurement path 2. A separation measurement path 4 extends from the connecting path 3 to a second air exit opening 41. In the separation measurement path 4 there is arranged a separation detector 42. The separation detector 42 is a gas chromatograph which, as a separation column 420, comprises a multi-capillary column. A large gas volume can be conducted through a multi-capillary column. In this way, it is possible for large amounts of sample gas to be conducted to the separation detector 42 and retained. The further components of the gas analysis apparatus 1 do not effect any retention. The path formed by the seeker measurement path 2, connecting path 3 and the section of the separation path between the connecting path 3 and separation detector 42 is referred to as "analytical path". The analytical path is free from valves, that is to say is without valves.

After approximately 30 seconds, all of the sample gas has been conducted through the separation detector 42, and the separation measurement path 4 has been purged by way of carrier gas, such that a new measurement of the individual concentrations can commence, without being biased by the preceding measurement. The separation detector 42 is furthermore designed to determine benzene concentrations with a sensitivity of 25 ppb.

As viewed from the connecting path 3, a second blower unit 43 is arranged downstream of the separation detector 42. The blower unit 43 generates a gas flow from the connecting path 3 through the separation detector 42 in the direction of the second air exit opening 41.

Furthermore, the separation measurement path 4 is connected to the carrier gas inlet opening 40, such that carrier gas can be conducted into the separation measurement path 4. At the carrier gas inlet opening 40, there is arranged a third blower unit 44 which generates a gas flow from the carrier gas inlet opening 40 in the direction of the separation measurement path 4.

From the connecting path 3, a filter path 6 branches off as a bypass with respect to the separation detector 42. The bypass connects the separation measurement path 4 to the connecting measurement path 3. Here, the separation measurement path 4 and the filter path 6 form a circuit.

The filter path 6 furthermore comprises a filter element 60. The filter element 60 is designed for filtering highly volatile compounds. When the carrier gas flows through the filter element 60, all highly volatile compounds are filtered, such that, after passing through the filter element 60, the carrier gas no longer contains any highly volatile compounds.

A valve 5 as a control element is arranged at the connection between the separation measurement path 4 and the filter path 6. The valve 5 is arranged upstream of the second air exit opening 41. The valve 5 switches between the filter path 6 and the second air exit opening 41. This means that, in one switching position, no gas flow through the second air exit opening 41 is permitted. In this case, the gas flow is introduced from the separation measurement path 4 into the filter path 6. In this embodiment, the second and the third blower unit 43, 44 together generate a more intense gas flow than the first blower unit 23. A part of the filtered carrier gas from the filter path 6 is in this case conducted into the separation measurement path 4, and purges the separation detector 42. Here, the carrier gas remains in the circuit formed by the separation measurement path 4 and the filter path 6.

The other part of the gas flow from the filter path 6 is conducted through the connecting measurement path 3 into the seeker measurement path 2. The first blower unit 23 is set such that it conducts the combined gas flow from the connecting measurement path 3 and from the seeker measurement path 2 out of the first air exit opening 21. This prevents the carrier gas from being blown out through the sample inlet opening 20.

When the valve 5 blocks the filter path 6, the circuit composed of separation measurement path 4 and filter path 6 is shut off. Furthermore, the carrier gas flowing in from the carrier gas inlet opening 40 is conducted directly to the second air exit opening 41. Thus, no gas is conducted from the filter path 6 into the connecting measurement path 3. In this way, sample gas now flows from the seeker measurement path 2 through the connecting measurement path 3. The flow direction of the gas flow in the connecting measurement path 3 is thereby reversed.

From the connecting measurement path 3, the sample gas flows into the separation measurement path 4 and thus through the separation detector 42. By means of the separation detector 42, different compounds in the sample gas mixture are separated, such that the concentration thereof can be detected separately. Since sample gas continues to flow in the seeker measurement path 2 from the sample gas inlet opening 20 to the first air exit opening 21, the seeker detector 22 continues to be supplied with sample gas. A situation in which the measurement by the seeker detector 22 is interrupted by the determination of the individual concentrations of the highly volatile compounds in the separation measurement path 4 is thus prevented.

Figure 2B:
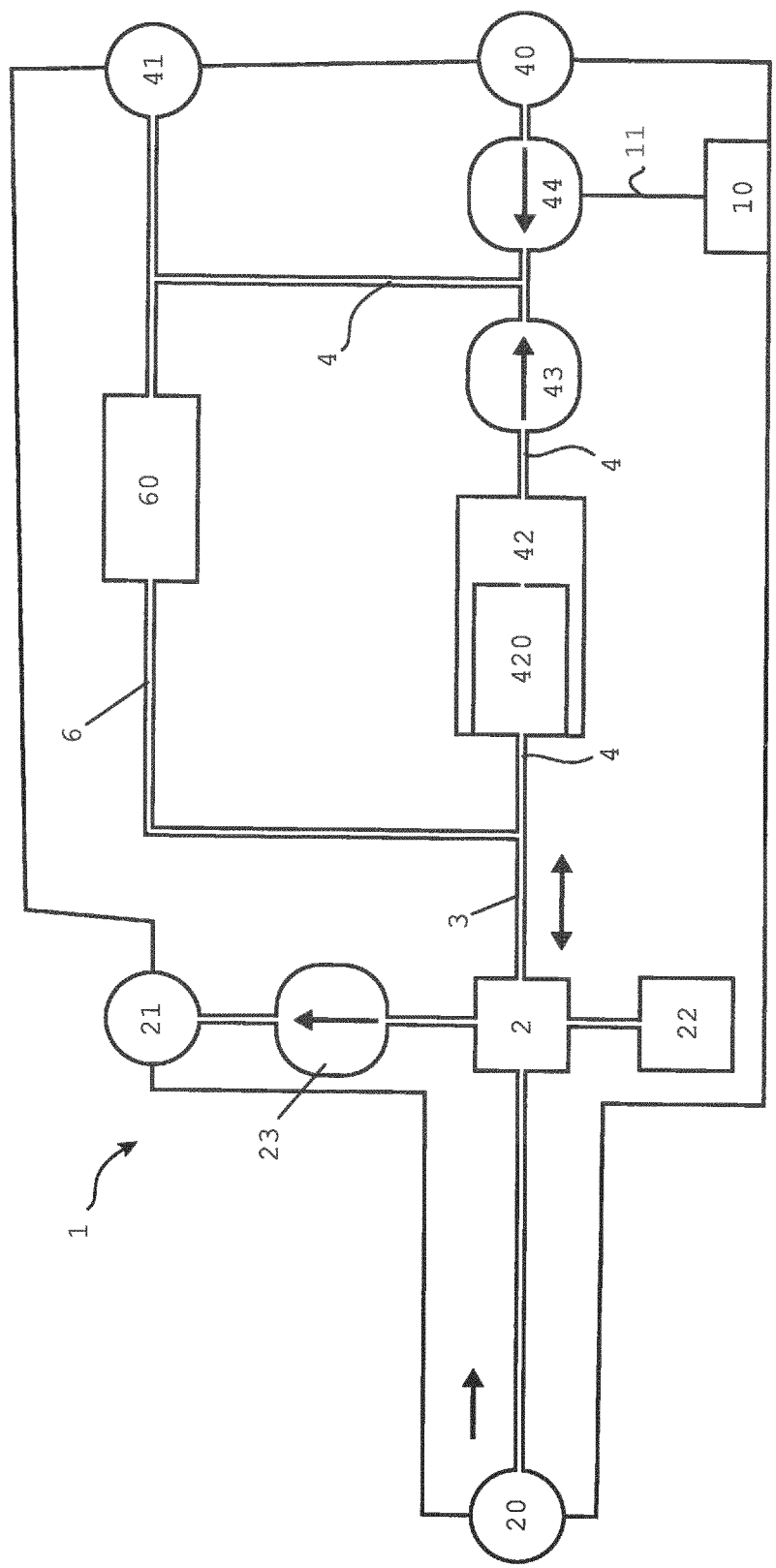

In a second preferred embodiment as per FIG. 2b, no valve is provided between the filter path 6 and the seeker measurement path 4. Rather, the control element is formed by the third regulable blower unit 44. The direction of the gas flow in the connecting measurement path 3 is, in this embodiment, controlled by the blower power of the third regulable blower unit 44. If the third regulable blower unit 44 is actuated at high power, the gas flow is conducted through the second air exit opening 41 and into the filter path 6. The blower power of the third regulable blower unit 44 is in this case high enough that the gas flow from the filter path 6 is conducted both into the connecting measurement path 3 and into the separation measurement path 4. To reverse the gas flow in the connecting measurement path 3, the power of the third regulable blower unit 44 is reduced to such an extent that no carrier gas, or only very little carrier gas, is introduced into the filter path 6. In this way, no carrier gas is introduced from the filter path 6 into the connecting measurement path 3. Rather, sample gas is conducted from the seeker measurement path 2 into the connecting measurement path 3, such that a reversal of the gas flow in the connecting measurement path 3 occurs.

In an alternative embodiment, the filter path 6 is not provided as a bypass with respect to the separation detector 42. In this embodiment, the separation measurement path 4 and the filter path 6 do not form a circuit. In this embodiment, the filter path 6 branches off from the connecting path 3 and extends as far as the carrier gas inlet opening 40. The filter path 6 comprises the filter element 60. The third blower unit 44, as control unit, is arranged at the carrier gas inlet opening 40. The third blower unit 44 conducts carrier gas from the carrier gas inlet opening 40 in the direction of the connecting path 3. The direction of the gas flow in the connecting path 3 can be controlled through regulated increase and decrease of the power of the third regulable blower unit 44.

It is also possible for the first regulable blower unit 23 or the second regulable blower unit 43 instead of the third regulable blower unit 44 to function as control element. Furthermore, it is also possible for a combination of the regulable blower units 23, 43, 44 to be utilized as control element. The blower units 23, 43, 44 function as flow generator elements.

In the embodiments in which the control element is formed by at least one of the regulable blower units 23, 43, 44, a throughflow sensor 45 may be provided at the carrier gas inlet opening 40. The throughflow sensor 45 measures the amount of carrier gas flowing into the separation measurement path 4 through the carrier gas inlet opening 40. The regulable blower units 23, 43, 44 may be controlled, in order to realize a reversal of the gas flow in the connecting path 3, on the basis of the throughflow rate of the carrier gas.

Figure 4A:
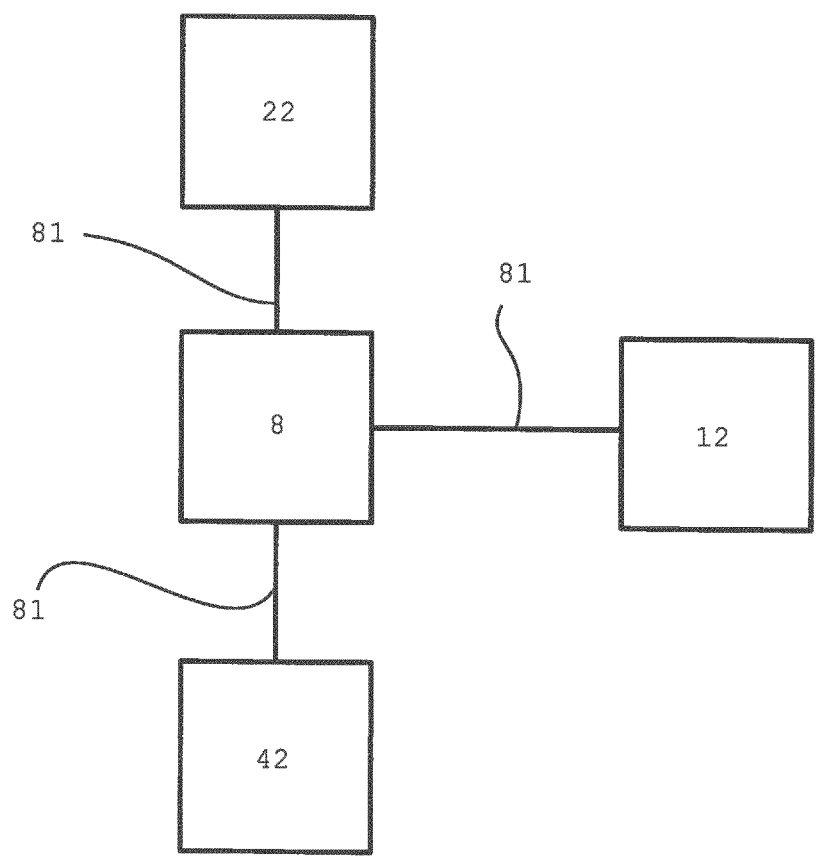
FIGS. 4a-c show a schematic illustration of an internal and external evaluation unit and the connection thereof to the detectors and possibly wireless connection to operating and display screen elements.
Figure 4B:
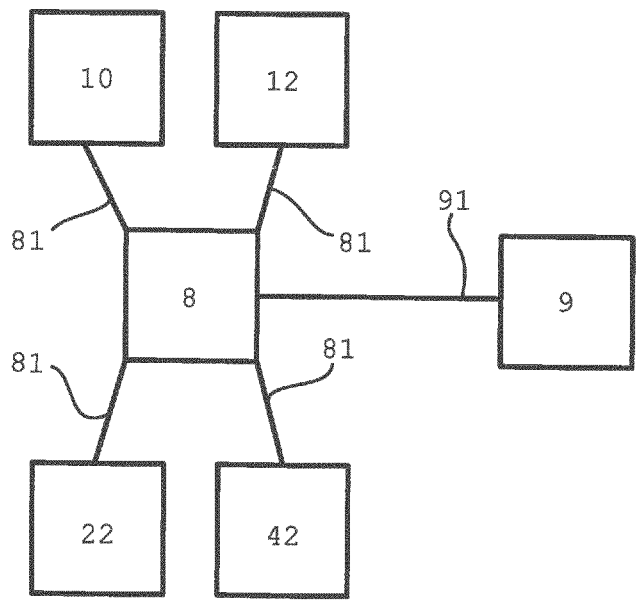
Figure 4C:
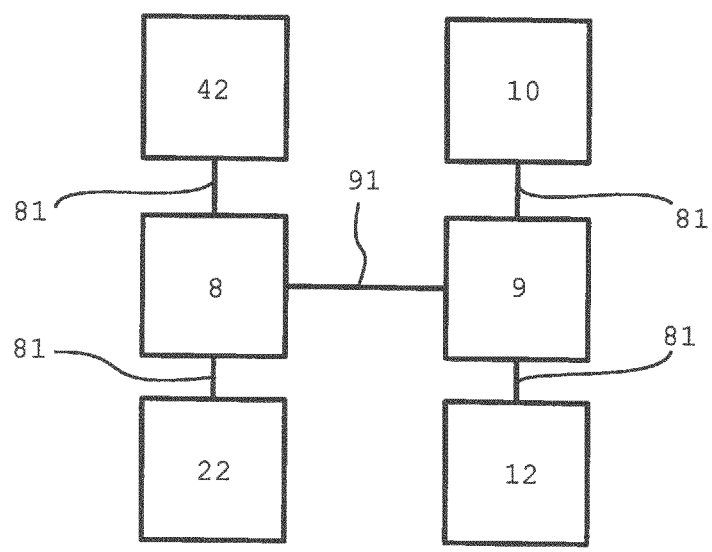

Furthermore, a location finding module 7 is provided which is designed to determine the geographical position of the portable gas analysis apparatus 1. The location finding module 7 is connected to the control element via a location finding signal line 71. Via the location finding signal line 71, the location finding module 7 can transmit the position signal to the control element. The position signal may then be stored in a memory unit (not illustrated), which is connected to an internal evaluation unit 8, along with the measurement data from the detectors 22, 42. Here, the detectors 22, 42 are connected to the internal evaluation unit 8 via data lines 81 (cf. FIG. 4). In this way, the measurement data from the detectors 22, 42 can be linked to the position data, such that spatial resolution of the measurement data is possible by way of multiple measurements at different geographical positions.

The operating element 10 is furthermore connected via an initiation signal line 11 to the control element. By means of the operating element 10, a user can manually demand a reversal of the gas flow in the connecting path 3. A measurement of the individual concentrations of the highly volatile compounds can be initiated in this way. Alternatively, the measurement of the individual concentrations may be initiated automatically when the seeker detector 22 detects an elevated total concentration of highly volatile compounds.

The detected measurement data may be transmitted from the evaluation unit 8 via a signal connection 81 to the display screen element 12. The display screen element 12 can display said measurement data to the user. The data of the measurement are thus provided to the user on site. The display screen element 12 is updated with a cycle of less than 1 second, that is to say it displays the present profile of the measurement by the separation detector 42 and/or by the seeker detector 22. It is thus possible after a measurement duration of approximately 10 seconds for the user to decide whether or not an evaluable set of data is available.

Figure 1B:
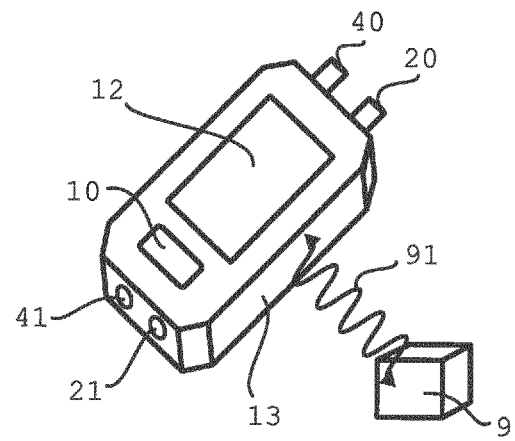

In a further embodiment, an external evaluation unit 9 may be provided in addition to the internal evaluation unit 8. The measurement data of the detectors 22, 42 are fed to the internal evaluation unit via data connections 81 and transmitted onward via a wireless connection 91 to the external evaluation unit 9. The operating element 10 and display screen element 12 are in this case connected via data connections 81 to the internal evaluation unit 8 and/or to the external evaluation unit 9. Exemplary embodiments of housings and signal connections are shown in FIG. 1b in conjunction with FIG. 4b or FIG. 1c in conjunction with FIG. 4c.

Figure 1C:
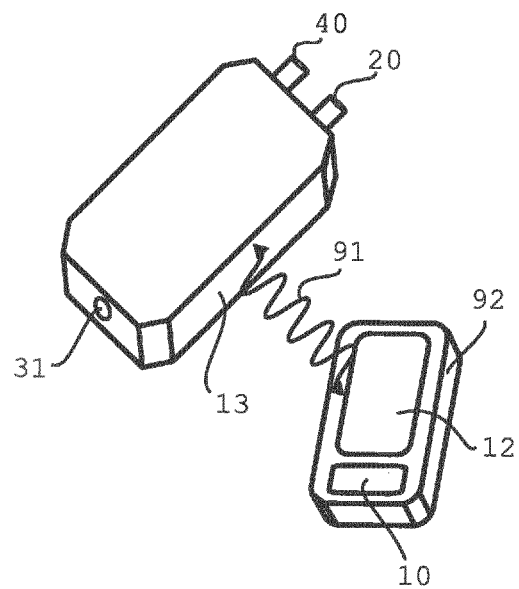
Figure 2C:
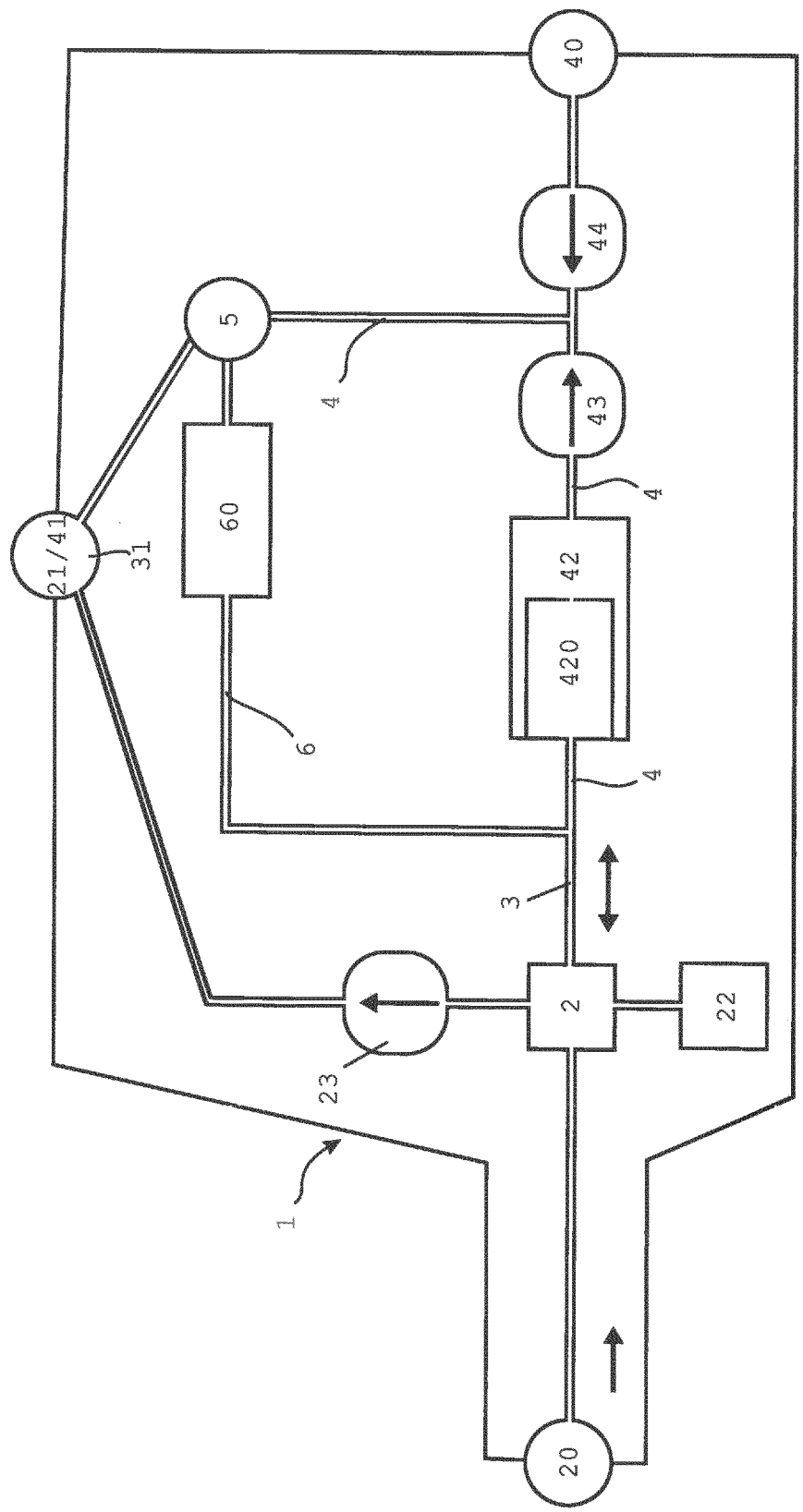
Figure 3:
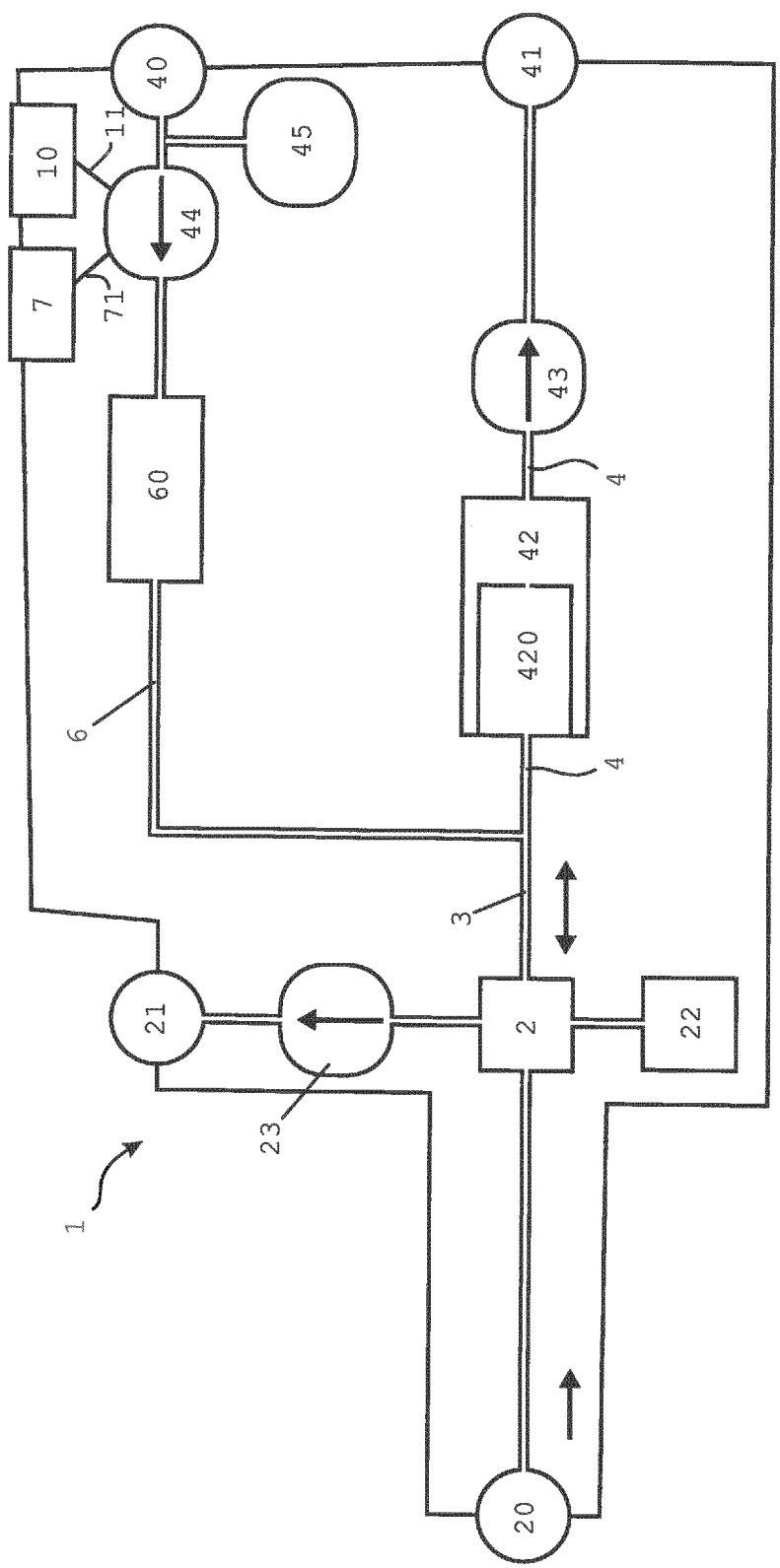
FIG. 3 shows a schematic illustration of the components in an alternative embodiment of the filter path.

It is pointed out that, if desired, the air exit openings 21, 41 may be combined to form a common air exit opening 31. This represents a further advantageous simplification and permits a very compact design, as shown in FIG. 1c and FIG. 2c.

For the determination of the individual concentrations of the highly volatile compounds, the gas flow in the connecting path 3 is reversed for approximately 1 second. The amount of sample gas extracted in this way is generally sufficient for a measurement by the separation detector 42. Owing to the short extraction time, a user can, using the gas analysis apparatus 1, seek out further locations where highly volatile compounds are suspected to exist and detect these by way of the seeker detector 22.

Figure 5A:
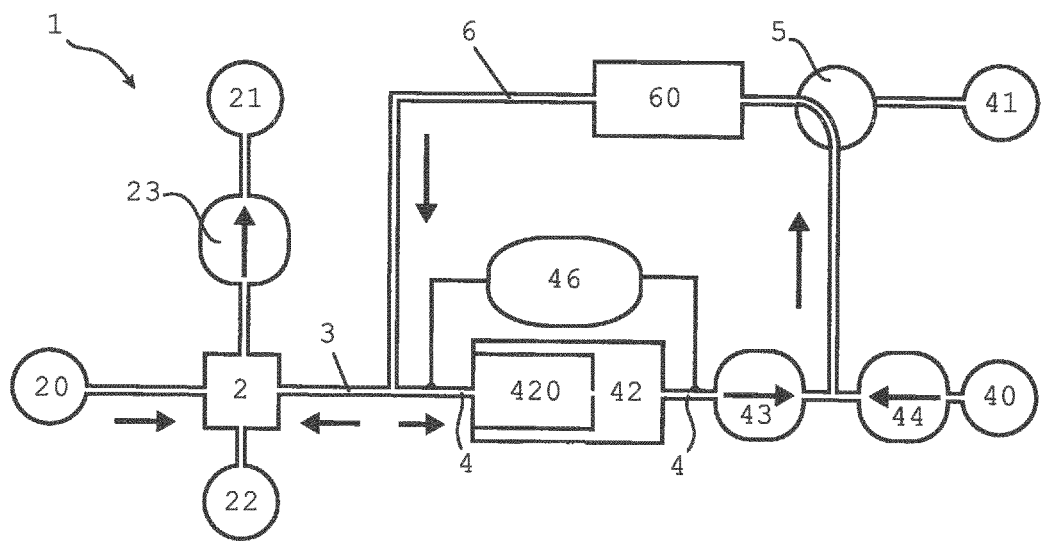
FIGS. 5a-b show a schematic illustration of the components and gas paths in an alternative embodiment with pressure difference sensor in two states in a manner dependent on a valve position.
Figure 5B:
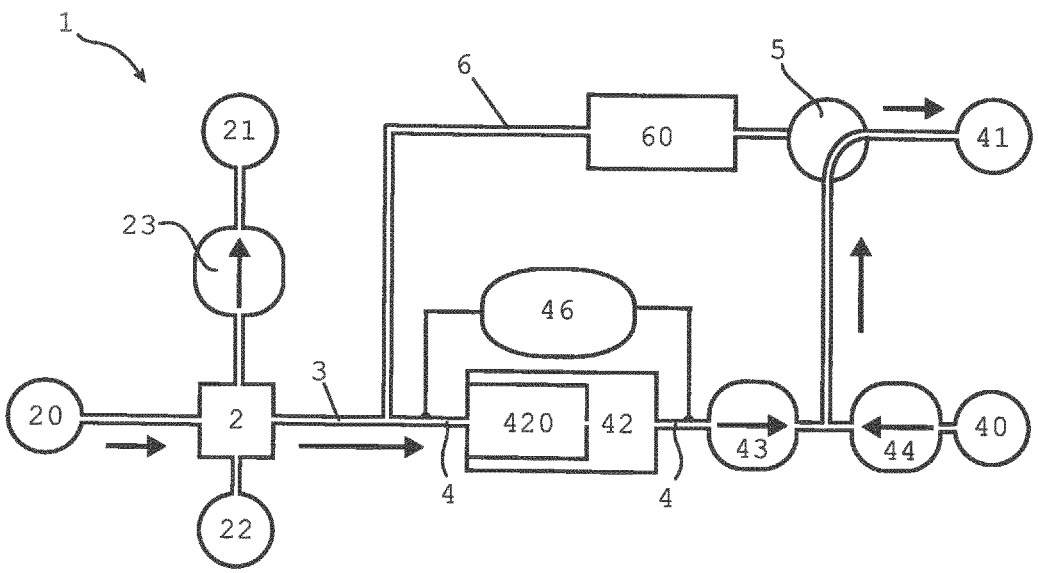

In an alternative embodiment, across the separation detector 42, there is arranged a throughflow or pressure difference sensor 46, wherein the gas flow generated by the regulable blower unit 43 is measured directly by a throughflow sensor or indirectly by a pressure difference sensor. The pressure difference is the direct cause of the gas flow. The blower 43 is regulated by the internal evaluation unit 8 in a manner dependent on the measurement at the pressure difference sensor 46. A blower unit 23 generates a continuous gas flow in the seeker measurement path 2 from the sample gas inlet opening 20 to the first air exit opening 21. For the injection of the separation measurement, the valve positioning and gas flows of which are schematically illustrated in FIG. 5b, the gas flow in the connecting piece 3 is directed from the seeker measurement path 2 into the separation measurement path 4, and thus sample gas is injected from the sample gas inlet opening 20 into the separation column 420 of the separation detector 42. In a different position at the valve 5, which is set before and after the injection, the separation measurement path 4 is purged with carrier gas, filtered in the filter 60, from the filter path 6, wherein the carrier gas can be merged with the gas flow from the separation detector to form an increased gas flow, as illustrated in FIG. 5a. The power of the regulable blower unit 43 is preferably regulated in a manner dependent on the measurement at the throughflow or pressure difference sensor 46, such that a predefined pressure difference and thus a certain gas flow through the separation column 420 is generated. If in each case identical gas flows are set during successive measurements, the measurements are better comparable.

Figure 6:
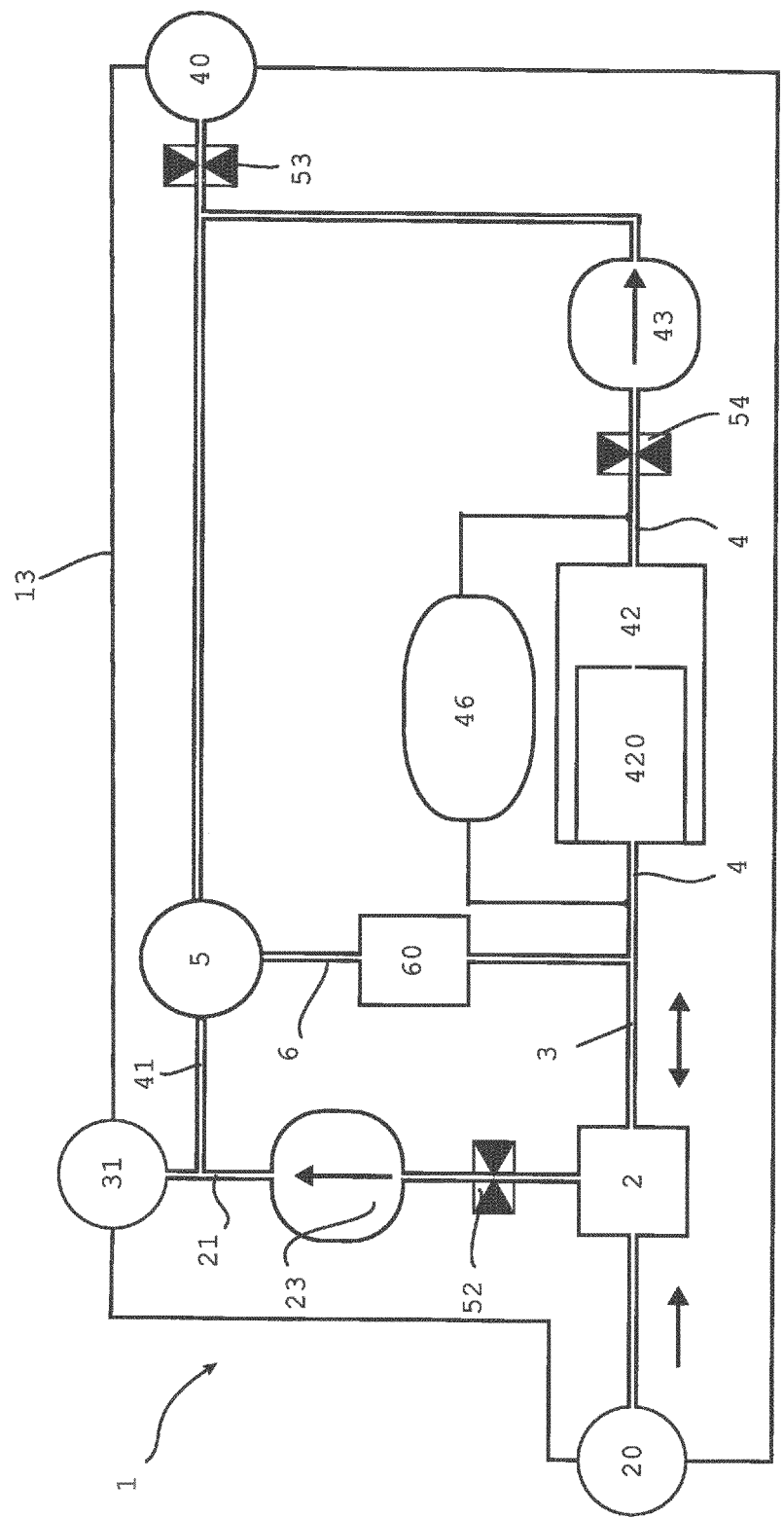
FIG. 6 shows a schematic illustration of the components and gas paths in a further alternative embodiment with gas path constrictions, pressure difference sensor and combined air exit opening.

In an alternative embodiment of the gas analysis apparatus, schematically illustrated in FIG. 6, the carrier gas inflow is implemented passively, that is to say without a third blower unit 44. Furthermore, the seeker measurement path 2 is optionally designed without a seeker detector 22. The omission of the third blower unit 44 and of the seeker detector 22 may possibly also be provided in the other embodiments. In this way, two active components are eliminated, whereby production costs, energy consumption, heat generation and risk of failure are reduced. The gas flow in the paths 2, 3, 4, 6, 21, 41 is determined by pressure differences, generated by the two blower units 23, 43, in the gas path system. Constrictions of the gas paths 52, 53, 54 are formed such that the throughflow is passively reduced, whereby the desired flow directions are realized with suitable speeds and without backflows. The gas path constrictions 52, 53, 54 may be formed by means of suitable diameters of the hoses or gas flow restrictions. A blower unit 23 generates a continuous gas flow in the seeker measurement path 2 from the sample gas inlet opening 20 via the first air exit opening 21 to the common air exit opening 31. In a first position at the valve 5, the carrier gas inlet opening 40 is connected to the filter path 6 and to the separation measurement path 4. The powers of the blowers 23, 43 and the diameters of the gas path constrictions are selected such that the gas flow in the connecting path 3 from the filter path 6 into the seeker measurement path 2 is greater than the gas flow from the filter path 6 into the separation measurement path 4. In this valve position, the volume formed from the circuit of separation measurement path 4 and filter path 6 has two connections, one to the connecting path 3 and one to the carrier gas inlet opening 40. Since the gas flow in the connecting path 3 is directed to the seeker measurement path 2, carrier gas is drawn in at the carrier gas inlet opening 40. The gas path constriction 53 additionally prevents a turbulent flow at this location, which could cause a brief backflow. A throughflow or pressure difference sensor 46 controls the state of the gas flow in the separation measurement path 4, wherein the power of the blower unit 43 is regulated in order to realize a certain gas flow. In a second position at the valve 5, the carrier gas inlet opening 40 and separation measurement path 4 are connected to the second air exit opening 41, and the connection to the filter path 6 is shut off. The gas flow from the sample gas inlet opening 20 is always directed toward the seeker measurement path 2 and from there via two paths to the common air exit opening 31. It is thus ensured that a closed-off sample volume is not contaminated or diluted, and gas exits the appliance only via the air exit openings 21, 41 or the common air exit opening 31. The first path runs out of the seeker measurement path 2 via the blower unit 23 and the first air exit opening 21. The second path runs via the seeker measurement path 2 into the now reversed flow in the connecting path into the separation measurement path 4, where sample gas is injected into the separation detector 42. In this second valve position, the gas flow at the carrier gas inlet opening 40 is also reversed, because there, a part of the gas flow flows out of the separation measurement path 4. In this embodiment, the carrier gas is preferably air, or the gas path constriction 53 is selected such that the carrier gas volume outside the carrier gas inlet opening 40 is not excessively contaminated by this flow from the separation measurement path 4. The major part of the exit air from the separation measurement path 4 flows into the second air exit opening 41. In the example, the two air exit openings 21, 41 are merged as a common air exit opening 31 at the housing 13. In this embodiment, it is also the case, with a small number of active components, that the advantages of the connection according to the invention of seeker measurement path 2 and separation measurement path 4 by the connecting path 3 are achieved, because these paths are all designed without valves, and the continuous operation of the blower 23 in the seeker, and in the second valve position the counter-purging with filtered carrier gas through the connecting path 3 into the seeker measurement path 2, each prevent an enrichment of the gas paths with volatile compounds. The continuous operation of the two blower units 23, 43 stabilizes the power thereof in relation to an activation process at the start of the measurement. By means of the regulation of the power of the blower 43 in a manner dependent on the measurement of the pressure difference sensor 46, the gas flow is further stabilized, and is influenced only by the position of the valve 5 outside the analytical path. The measurement appliance thus exhibits altogether very stable operation, whereby successive measurements and also signal values within one measurement at the separation detector are better comparable. In the second valve position, the appliance is in a standby mode, in which there is always a gas flow from the sample gas inlet opening 20 into the seeker measurement path 2. After the triggering of the separation measurement at the operating element 10, the valve 5 is switched, and the flow in the connecting path 3 is reversed, without delay, such that sample gas is injected directly from the controlled gas flow in the seeker measurement path 2 into the separation measurement path 4, and the separation measurement begins. Approximately one second elapses between the triggering of the measurement and the end of the injection. Without the seeker, the sample would have to be injected from a static volume outside the appliance, which is a more time-consuming and less easily controllable solution.

The invention claimed is:

1. A portable gas analysis apparatus comprising a seeker measurement path and a separation measurement path, wherein the seeker measurement path extends from a sample inlet opening to a first air exit opening, wherein a connecting path branches off from the seeker measurement path to the separation measurement path, and the separation measurement path extends from the connecting path to a second air exit opening and is connected to a carrier gas inlet opening, wherein a separation detector is arranged at the separation measurement path, wherein the gas analysis apparatus has a control element configured for reversing the gas flow in the connecting path such that, in case of flow being reversed, a first part of a sample gas mixture entering at the sample inlet opening flows via the connecting path into the separation measurement path and a second part of the sample gas mixture remains in the seeker measurement path.

2. The portable gas analysis apparatus of claim 1, wherein the separation detector is configured for determining an amount of highly volatile compounds.

3. The portable gas analysis apparatus of claim 1, wherein the separation detector comprises a separation column, and the separation column is a multi-capillary column.

4. The portable gas analysis apparatus of claim 1, wherein the seeker measurement path, the separation measurement path as far as the separation detector, and the connecting path are in each case of valves.

5. The portable gas analysis apparatus of claim 1, wherein, in the seeker measurement path, there is arranged a seeker detector which is configured for continuous detection of a group of highly volatile compounds.

6. The portable gas analysis apparatus of claim 1, wherein the first air exit opening and the second air exit opening are combined within one housing to form a common air exit opening.

7. The portable gas analysis apparatus of claim 1, wherein a filter path branches off from the connecting path, wherein a filter element is arranged in the filter path, and the filter path is connected to the carrier gas inlet opening.

8. The portable gas analysis apparatus of claim 7, wherein the control element is a valve configured for opening and shutting off the filter path.

9. The portable gas analysis apparatus of claim 1, wherein the control element a regulable blower unit at the carrier gas inlet opening, at the first air exit opening, or at the separation detector.

10. The portable gas analysis apparatus of claim 1, wherein the apparatus is configured to determine pressure differences along gas paths of blower units and gas path constrictions, and the apparatus comprises a valve that defines a direction of gas flow in the connecting path.

11. The portable gas analysis apparatus of claim 1, wherein, across the separation measurement path, there is arranged a throughflow or pressure difference sensor, wherein power of a blower unit at the separation detector is regulated based on measurements by the throughflow or pressure difference sensor.

12. A system comprising the portable gas analysis apparatus of claim 1 and an external evaluation unit, wherein the apparatus comprises an internal evaluation unit, and the internal evaluation unit and the external evaluation unit are configured for exchanging control commands and measurement data by way of a wireless signal connection.

13. The portable gas analysis apparatus of claim 2, wherein the separation detector is a gas chromatograph with a photoionisation detector, a heat conductivity detector, a semiconductor gas detector, or a mass spectrometer.

14. The portable gas analysis apparatus of claim 5, wherein the seeker detector is a photoionisation detector, a semiconductor gas detector, or a heat conductivity detector.

15. The portable gas analysis apparatus of claim 1, wherein the control element is a regulable blower unit at the carrier gas inlet opening, at the first air exit opening, and at the separation detector.

16. A gas analysis method performed by a portable gas analysis apparatus that includes a seeker measurement path and a separation measurement path, in which the seeker measurement path extends from a sample inlet opening to a first air exit opening, a connecting path branches off from the seeker measurement path to the separation measurement path, the separation measurement path extends from the connecting path to a second air exit opening and is connected to a carrier gas inlet opening, a separation detector is arranged at the separation measurement path, and that includes a control element configured for reversing the gas flow in the connecting path such that, in case of flow being reversed, a first part of a sample gas mixture entering at the sample inlet opening flows via the connecting path into the separation measurement path and a second part of the sample gas mixture remains in the seeker measurement path, the method comprising:
  setting a higher pressure in the separation measurement path than in the seeker measurement path,
  detecting the presence of a highly volatile compound from a group of highly volatile compounds,
  setting a lower pressure in the separation measurement path than in the seeker measurement path, and
  separating individual members of the group of highly volatile compounds.

17. The gas analysis method of claim 16, wherein the detecting of the presence of the highly volatile compound is performed continuously during the separation process and a determination processes that determines an amount of the separated individual members of the group of highly volatile compounds.

* * * * *